United States Patent
Robinson et al.

(10) Patent No.: US 10,396,180 B2
(45) Date of Patent: Aug. 27, 2019

(54) METHOD FOR FORMING APPARATUS COMPRISING TWO DIMENSIONAL MATERIAL

(71) Applicant: EMBERION OY, Espoo (FI)

(72) Inventors: Adam Robinson, Cambridge (GB);
Darryl Cotton, St. Ives (GB);
Alexander Bessonov, Cambridge (GB);
Richard White, Huntingdon (GB);
Yinglin Liu, Cambridge (GB)

(73) Assignee: EMBERION OY, Espoo (FI)

( * ) Notice: Subject to any disclaimer, the term of this patent is extended or adjusted under 35 U.S.C. 154(b) by 0 days.

(21) Appl. No.: 15/754,460

(22) PCT Filed: Aug. 25, 2016

(86) PCT No.: PCT/EP2016/070124
§ 371 (c)(1),
(2) Date: Feb. 22, 2018

(87) PCT Pub. No.: WO2017/032850
PCT Pub. Date: Mar. 2, 2017

(65) Prior Publication Data
US 2018/0248019 A1 Aug. 30, 2018

(30) Foreign Application Priority Data
Aug. 25, 2015 (EP) .................... 15182390

(51) Int. Cl.
*H01L 21/00* (2006.01)
*H01L 29/66* (2006.01)
(Continued)

(52) U.S. Cl.
CPC .... *H01L 29/66742* (2013.01); *H01L 29/1606* (2013.01); *H01L 29/42364* (2013.01);
(Continued)

(58) Field of Classification Search
CPC ............. H01L 29/66742; H01L 31/028; H01L 31/0236; H01L 31/0352; H01L 31/112;
(Continued)

(56) References Cited

U.S. PATENT DOCUMENTS

| 2013/0032782 A1 | 2/2013 | Gerasimos et al. |
| 2014/0299741 A1 | 10/2014 | Colli |

(Continued)

FOREIGN PATENT DOCUMENTS

| EP | 2 620 982 A2 | 7/2013 |
| EP | 2 752 880 A2 | 7/2014 |

(Continued)

OTHER PUBLICATIONS

PCT International Preliminary Report on Patentability dated Feb. 27, 2018 corresponding to International Patent Application No. PCT/EP2016/070124.

(Continued)

*Primary Examiner* — Caleb E Henry
(74) *Attorney, Agent, or Firm* — Squire Patton Boggs (US) LLP

(57) ABSTRACT

A method and apparatus, the method comprising: forming at least two electrodes (23) on a release layer wherein the at least two electrodes are configured to enable a layer of two dimensional material (25) to be provided between the at least two electrodes; providing moldable polymer (27) overlaying the at least two electrodes; wherein the at least two electrodes and the moldable polymer form at least part of a planar surface (29).

8 Claims, 11 Drawing Sheets

Figure 1:
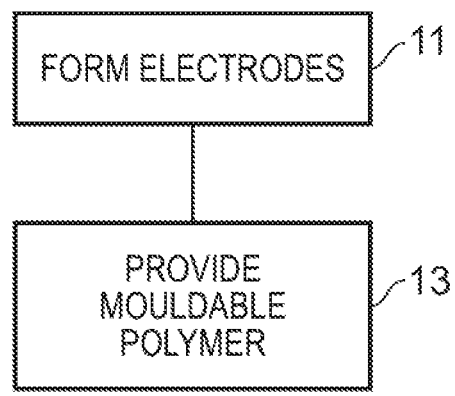

(51) Int. Cl.
*H01L 29/778* (2006.01)
*H01L 31/028* (2006.01)
*H01L 31/0352* (2006.01)
*H01L 31/113* (2006.01)
*H01L 29/16* (2006.01)
*H01L 29/423* (2006.01)
*G01N 27/414* (2006.01)

(52) U.S. Cl.
CPC ...... *H01L 29/66045* (2013.01); *H01L 29/778* (2013.01); *H01L 31/028* (2013.01); *H01L 31/035218* (2013.01); *H01L 31/1136* (2013.01); *G01N 27/4146* (2013.01); *Y02E 10/547* (2013.01)

(58) Field of Classification Search
CPC ......... H01L 31/18; H01L 29/16; H01L 29/06; G01N 27/414
USPC ........................................................ 438/151
See application file for complete search history.

(56) References Cited

U.S. PATENT DOCUMENTS

2018/0261672 A1* 9/2018 Cotton .............. H01L 29/66045
2018/0261702 A1* 9/2018 Bessonov ......... H01L 31/02363

FOREIGN PATENT DOCUMENTS

| JP | 2007-73857 A | 3/2007 |
| JP | 2010-62399 A | 3/2010 |
| JP | 2011-101030 A | 5/2011 |
| KR | 20140090021 A | 7/2014 |
| KR | 20150063177 A | 6/2015 |

OTHER PUBLICATIONS

International Search Report & Written Opinion dated Jan. 23, 2017 corresponding to International Patent Application No. PCT/EP2016/070124.
May 23, 2016 Search Report issued in European Patent Application No. 15182390.

* cited by examiner

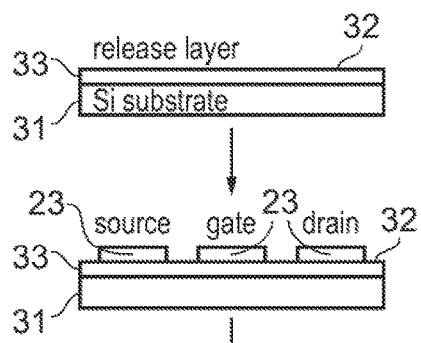
FIG. 5A
FIG. 5B
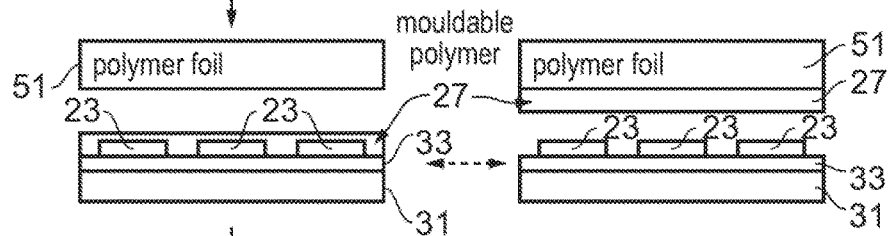
FIG. 5C
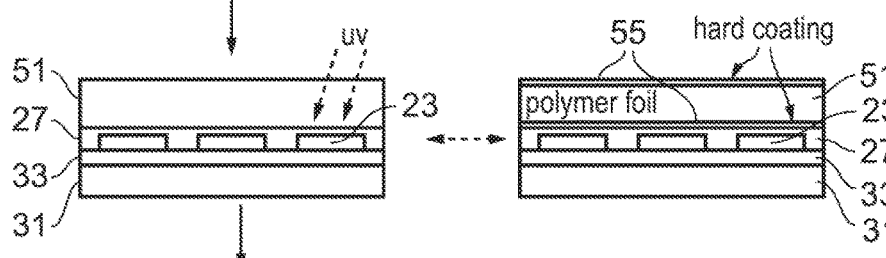
FIG. 5D
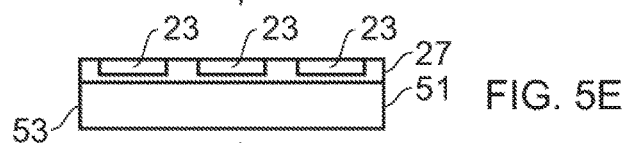
FIG. 5E
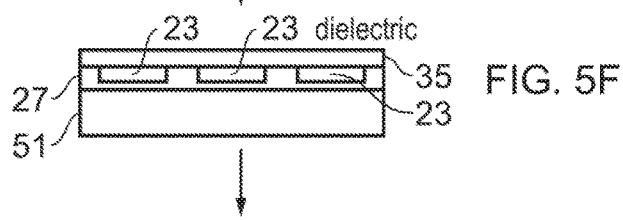
FIG. 5F

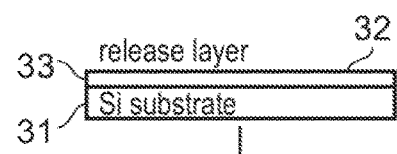
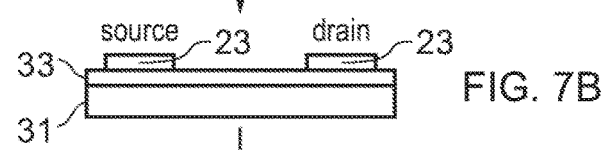
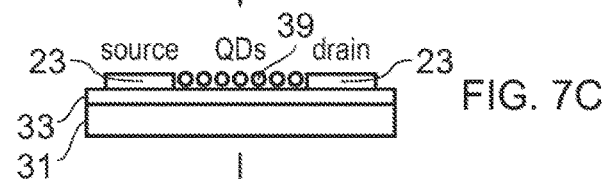
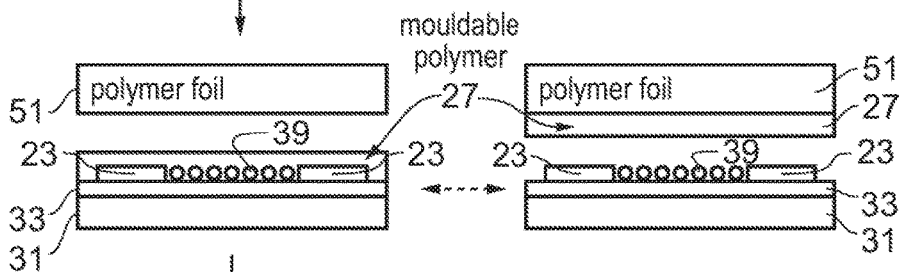
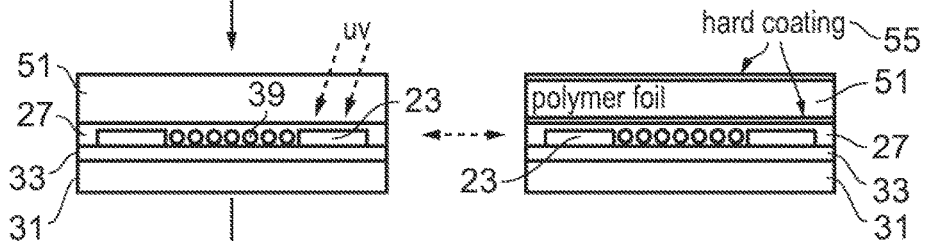
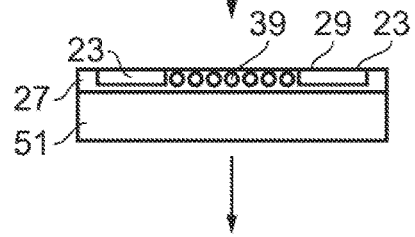

METHOD FOR FORMING APPARATUS COMPRISING TWO DIMENSIONAL MATERIAL

TECHNOLOGICAL FIELD

Examples of the disclosure relate to a method for forming apparatus comprising two dimensional material. In particular, they relate to a method for forming electronic apparatus comprising two dimensional material such as graphene.

BACKGROUND

Apparatus comprising two dimensional materials such as graphene are well known. For instance graphene can be provided in devices such as resistive sensors or field effect transistors to enable parameters such as chemicals or light to be detected. In other devices graphene field effect transistors can be used as logic elements or other electronic components.

It is useful to provide improved methods of forming such devices.

BRIEF SUMMARY

According to various, but not necessarily all, examples of the disclosure there may be provided a method comprising: forming at least two electrodes on a release layer wherein the at least two electrodes are configured to enable a layer of two dimensional material to be provided between the at least two electrodes; providing mouldable polymer overlaying the at least two electrodes; wherein the at least two electrodes and the mouldable polymer form at least part of a planar surface.

In some examples the release layer may have a smooth surface to enable a smooth layer of two dimensional material to be provided.

In some examples the at least two electrodes may be provided in the same plane.

In some examples the method may comprise providing the two dimensional material overlaying the electrodes after the electrodes have been removed from the release layer.

In some examples the method may comprise providing the two dimensional material on the release layer. The method may also comprise providing at least part of the at least two electrodes overlaying the two dimensional material. The at least two electrodes, the two dimensional material and the mouldable polymer may form at least part of the planar surface.

In some examples the method may comprise forming a composite polymer substrate comprising the mouldable polymer. The method may also comprise providing hard coating on the composite polymer substrate.

In some examples the two dimensional material and the at least two electrodes may form at least part of a bottom gate field effect transistor.

In some examples the two dimensional material and the at least two electrodes form at least part of a top gate field effect transistor.

In some examples the method may comprise providing a plurality of electrodes and portions of two dimensional materials to form a plurality of field effect transistors wherein at least some the field effect transistors are bottom gate field effect transistors and at least some of the field effect transistors are top gate field effect transistors.

In some examples the two dimensional material may comprise graphene.

In some examples the method may comprise activating the two dimensional material.

In some examples the method may comprise activating the two dimensional material with quantum dots.

In some examples the mouldable polymer may provide a flexible substrate for the at least two electrodes after the at least two electrodes are removed from the release layer.

In some examples the mouldable polymer may comprise at least one of, liquid polymer, mouldable polymer foil.

According to various, but not necessarily all, examples of the disclosure there may be provided an apparatus formed by any of the methods described above.

According to various, but not necessarily all, examples of the disclosure there may be provided an apparatus comprising: at least two electrodes and a layer of two dimensional material wherein the at least two electrodes were formed on a release layer and the at least two electrodes are configured to enable the layer of two dimensional material to be provided between the at least two electrodes; and mouldable polymer overlaying the at least two electrodes; wherein the at least two electrodes and the mouldable polymer form at least part of a planar surface.

In some examples the release layer may be a smooth surface to enable a smooth layer of two dimensional material to be provided.

In some examples the at least two electrodes may be provided in the same plane.

In some examples the two dimensional material may be provided overlaying the electrodes after the electrodes have been removed from the release layer.

In some examples the two dimensional material may be provided on the release layer. At least part of the at least two electrodes may be provided overlaying the two dimensional material. The at least two electrodes, the two dimensional material and the mouldable polymer may form at least part of the planar surface.

In some examples the apparatus may comprise a polymer substrate comprising the mouldable polymer. In some examples the apparatus may comprise a hard coating on the composite polymer substrate.

In some examples the two dimensional material and the at least two electrodes may form at least part of a bottom gate field effect transistor.

In some examples the two dimensional material and the at least two electrodes may form at least part of a top gate field effect transistor.

In some examples the apparatus may comprise a plurality of electrodes and portions of two dimensional materials which form a plurality of field effect transistors wherein at least some the field effect transistors are bottom gate field effect transistors and at least some of the field effect transistors are top gate field effect transistors.

In some examples the two dimensional material may comprise graphene.

In some examples the two dimensional material may be activated.

In some examples the two dimensional material may be activated with quantum dots.

In some examples the mouldable polymer may provide a flexible substrate for the at least two electrodes after the at least two electrodes are removed from the release layer In some examples the mouldable polymer may comprise at least one of, liquid polymer, mouldable polymer foil.

According to various, but not necessarily all, examples of the disclosure there is provided examples as claimed in the appended claims.

BRIEF DESCRIPTION

Figure 2:
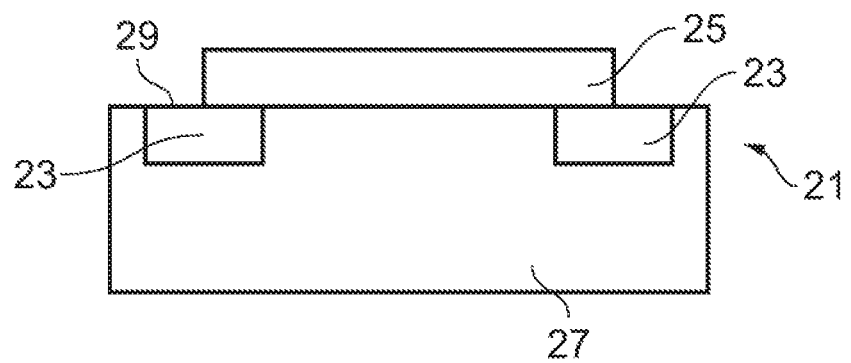
Figure 8:
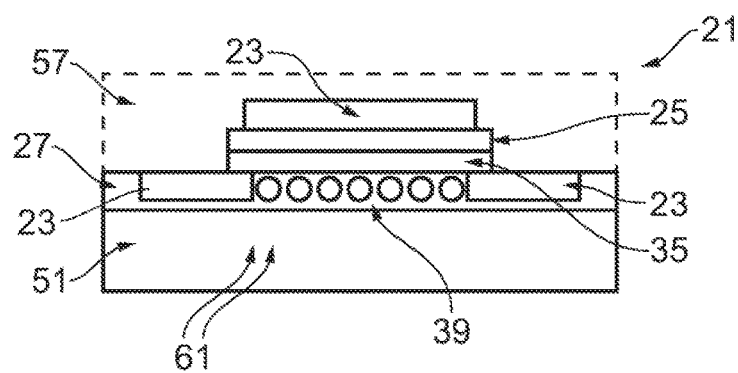
Figure 9:
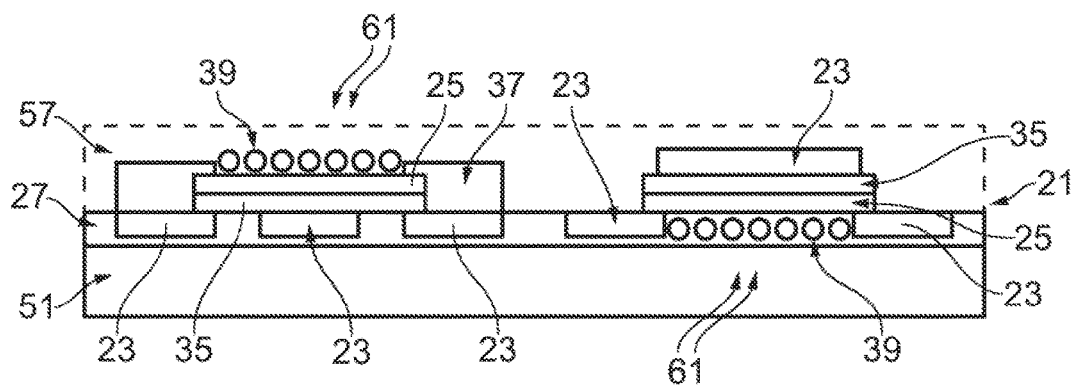

For a better understanding of various examples that are useful for understanding the detailed description, reference will now be made by way of example only to the accompanying drawings in which:

FIG. 1 illustrates a method;
FIG. 2 illustrates an apparatus;
FIGS. 3A to 3G illustrate an example method:
FIGS. 4A to 4I illustrate an example method;
FIGS. 5A to 5K illustrate an example method;
FIG. 6 illustrates an apparatus;
FIGS. 7A to 7K illustrate an example method;
FIG. 8 illustrates an apparatus; and
FIG. 9 illustrates an apparatus.

DETAILED DESCRIPTION

The Figures illustrate example methods and apparatus. The methods may be used to form apparatus comprising two dimensional material. The apparatus may form electronic components within electronic devices. In some examples the apparatus which are formed may be for sensing. The apparatus may be for sensing environmental parameters such as light, temperature, chemicals or other parameters. The apparatus may be for active sensing or for passive sensing. The apparatus may be a photodetector and may be used for imaging. The apparatus may sense light only at a first wavelength or only within a first range of wavelengths.

FIG. 1 illustrates a method according to examples of the disclosure. The method may be used to form apparatus 21 comprising one or more electronic components where the electronic components comprise a two dimensional material such as graphene.

The method comprises, at block 11 forming at least two electrodes 23 on a release layer 33. The at least two electrodes 23 are configured to enable a layer of two dimensional material 25 to be provided between the at least two electrodes 23. The method also comprises, at block 13, providing mouldable polymer 27 overlaying the at least two electrodes 23. The at least two electrodes 23 and the mouldable polymer 27 form at least part of a planar surface 29.

It is to be appreciated that the electrodes 23 and the two dimensional material 25 may have any configuration which enables an electronic component to be formed. Example methods for forming field effect transistor (FET) devices are illustrated in more detail in FIGS. 3A to 9. Other methods for forming other types of devices may be used in other examples of the disclosure.

FIG. 2 illustrates an example apparatus 21 which may be formed using methods such as the method of FIG. 1. The example apparatus 21 comprises at least two electrodes 23 and a layer of two dimensional material 25. The at least two electrodes 23 were formed on a release layer 33. The at least two electrodes 23 are configured to enable the layer of two dimensional material 25 to be provided between the at least two electrodes 23. The apparatus 21 also comprises mouldable polymer 27 overlaying the electrodes 23. The at least two electrodes 23 and the mouldable polymer 27 form at least part of a planar surface 29.

In the example of FIG. 2 the apparatus 21 comprises two electrodes 23. In this example the layer of two dimensional material 25 may be provided between the two electrodes 23 to form an electronic device such as a resistive sensor. It is to be appreciated that other arrangements of the layer of two dimensional material 25 and the electrodes 23 may be provided in other examples. For instance, in some examples the apparatus 21 may comprise three electrodes 23 to enable FET devices to be provided.

The electrodes 23 may comprise any suitable conductive material. The electrodes 23 may be electrically connected to the two dimensional material 25. The electrodes 23 may be electrically connected to the two dimensional material 25 to enable direct current to flow through the electrodes 23 and the two dimensional material 25.

In the example of FIG. 2 both of the electrodes 23 are provided on the same plane. Forming the electrodes 23 on the same release layer 33 may ensure that the electrodes 23 are provided within the same plane. This reduces the number of step edges in the apparatus 21.

The mouldable polymer 27 is provided overlaying the electrodes 23. The mouldable polymer 27 may be deposited overlaying the electrodes on the release layer 33. The mouldable polymer 27 may comprise any polymer material which is fluid enough to embed the electrodes 23. Once the mouldable polymer 27 is provided around the electrodes 23 the mouldable polymer 27 may be cured or otherwise hardened. Once the mouldable polymer 27 has hardened it may form a flexible substrate for the at least two electrodes 23. The mouldable polymer 27 may form a thin flexible substrate.

Depositing the mouldable polymer 27 on the same release layer as the electrodes 23 may enable the mouldable polymer 27 and the electrodes 23 to form at least part of a planar surface 29. The planar surface 29 may comprise a smooth flat surface. The release layer 33 may comprise a material having a smooth flat surface to ensure that the planar surface 29 is also smooth and flat. The other electronic components of the apparatus 21 such as the layer of two dimensional material 25 or electrical connections to the layer of two dimensional material 25 may be deposited on the planar surface 29.

The layer of two dimensional material 25 may comprise a very thin layer of material. In some examples the layer of two dimensional material 25 could be an atomic monolayer. In some examples the layer of two dimensional material 25 could comprise several atomic monolayers. The layer of two dimensional material 25 could comprise graphene, molybdenum disulphide, boron nitride or any other suitable material.

In the example apparatus 21 of FIG. 2 the layer of two dimensional material 25 is provided overlaying at least part of the electrodes 23. The two dimensional material 25 may be provided overlaying the electrodes 23 after the electrodes 23 have been removed from the release layer 33. In other examples the two dimensional material 25 could also be formed or deposited on the release layer 33 along with the electrodes 23.

The layer of two dimensional material 25 is provided on the planar surface 29. As a smooth flat surface is provided for the two dimensional material 25 this reduces the amount of discontinuities and/or impurities in the two dimensional material 25 and may provide for improved charge transfer characteristics of the two dimensional material 25.

FIGS. 3A to 3G illustrate example methods which may be used to form other example apparatus 21. The example method of FIGS. 3A to 3G comprises forming a mouldable polymer 27 substrate with a plurality of embedded electrodes 23. The mouldable polymer 27 and the embedded electrodes 23 form a planar surface 29 which can then be used for depositing graphene or any other suitable two dimensional material 25.

Figure 3A:
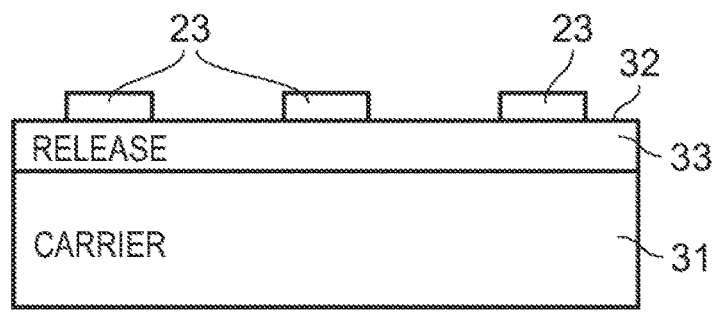

In FIG. 3A a release layer 33 is provided on a carrier substrate 31. In the example of FIG. 3A the carrier substrate 31 may provide a rigid or substantially rigid substrate which may provide support while the electrodes 23 and/or other components of the apparatus 21 are being fabricated on the release layer 33. The carrier substrate 31 may comprise a silicon wafer or any other suitable material.

The carrier substrate 31 may be flat or substantially flat.

The release layer 33 is provided overlaying the carrier substrate 31. The release layer 33 may comprise a sacrificial layer which may enable the components of the apparatus 21 that are fabricated to be removed from the carrier substrate 31. The material that is used for the release layer 33 may depend on the components that are being fabricated and the material that is being used for those components. In some examples the release layer 33 may comprise copper or any other suitable material.

The release layer 33 may have a smooth surface 32. The components of the apparatus 21 may be formed on the smooth surface 32 of the release layer 33 so that the components of the apparatus 21 form a planar surface 29. The release layer 33 has a surface which is smooth enough to enable a smooth layer of two dimensional material 25 to be provided. The two dimensional material 25 could be provided on the release layer 33 or on a planar surface 29 which has been formed on the release layer 33.

In FIG. 3A the electrodes 23 are deposited on the release layer 33. In the example of FIG. 3A three electrodes 23 are provided. The three electrodes 23 may form a source, gate and drain electrode for an FET. Each of the electrodes 23 are provided in the same plane. This reduces the number of step edges in the apparatus 21. It is to be appreciated that other arrangements of electrodes may be used in other examples of the disclosure.

The electrodes 23 may comprise any conductive material such as a metal.

The electrodes 23 may be deposited using any suitable technique. For instance the electrodes 23 could be formed by photolithography followed by thermal or electron beam evaporation of a metal, or any other suitable process.

Figure 3B:
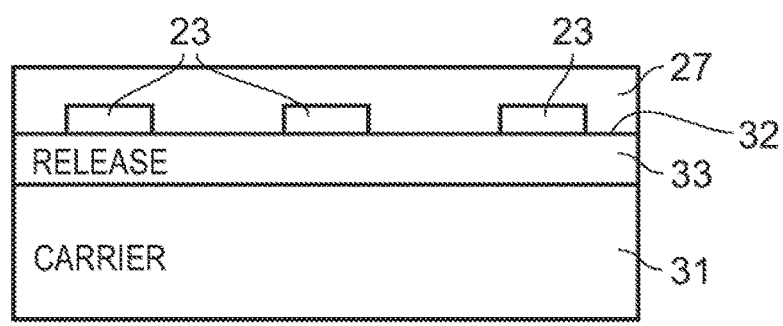

In FIG. 3B mouldable polymer 27 is provided overlaying the electrodes 23. The mouldable polymer 27 is deposited on the release layer 33 overlaying the electrodes 23. The mouldable polymer 27 comprises any polymer which will embed the electrodes 23 and form a planar surface 29 against the surface 32 of the release layer 33.

In some examples the mouldable polymer 27 may comprise a liquid polymer which may be deposited onto the release layer 33 via spin coating, spray coating or any other suitable process. In other examples the mouldable polymer 27 may comprise a polymer foil which may be deposited by hot embossing or any other suitable process.

Figure 3C:
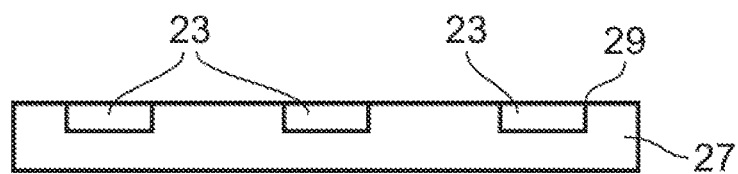

In FIG. 3C the carrier substrate 31 and release layer 33 are removed. The mouldable polymer 27 may be hardened or cured before the carrier substrate 31 and release layer 33 are removed so that the mouldable polymer 27 provides a substrate for the electrodes 23. The mouldable polymer 27 may provide a flexible substrate for the electrodes 23. The mouldable polymer 27 may enable further components of the apparatus 21 to be fabricated overlaying the electrodes 23.

The mouldable polymer 27 and the electrodes 23 form a planar surface 29. The planar surface 29 may be smooth and flat. The planar surface 29 may be a uniform or substantially uniform surface.

Figure 3D:
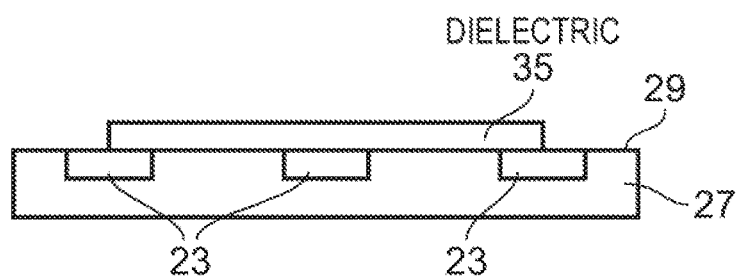

The other components of the apparatus 21 may be fabricated on the planar surface 29 formed by the mouldable polymer 27 and the electrodes 23. In FIG. 3D a dielectric 35 is provided on the planar surface 29. In the example of FIG. 3D the dielectric 35 is provided overlaying the gate electrode 23 and at least part of the source and drain electrodes 23.

The dielectric 35 may comprise any suitable insulating material. In some examples the dielectric 35 may comprise aluminum oxide which could be deposited using atomic layer deposition or any other suitable process. The dielectric 35 may be provided in a thin layer.

Figure 3E:
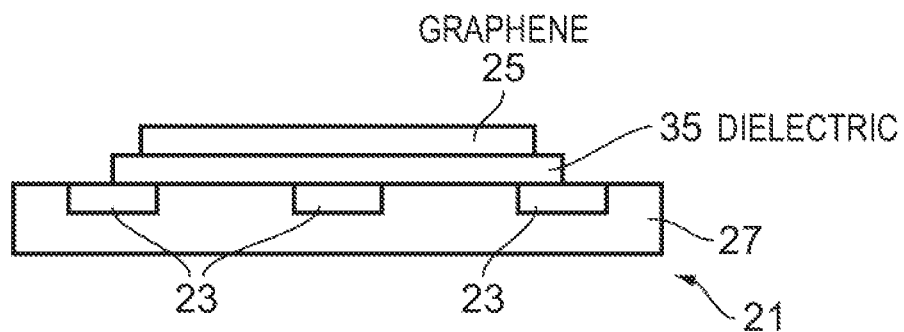

In FIG. 3E a layer of two dimensional material 25 is deposited on to the planar surface 29. In the example of FIGS. 3A to 3G the two dimensional material 25 comprises graphene.

The graphene may be deposited on to the planar surface 29 using any suitable technique. In some examples the graphene may be formed on a separate substrate and transferred onto the planar surface 29. The graphene may then be patterned using photolithography, plasma etching or any other suitable process.

In the example of FIG. 3E the graphene is provided overlaying the dielectric 35 so that the dielectric 35 forms an insulating barrier between the graphene and the electrodes 23.

Figure 3F:
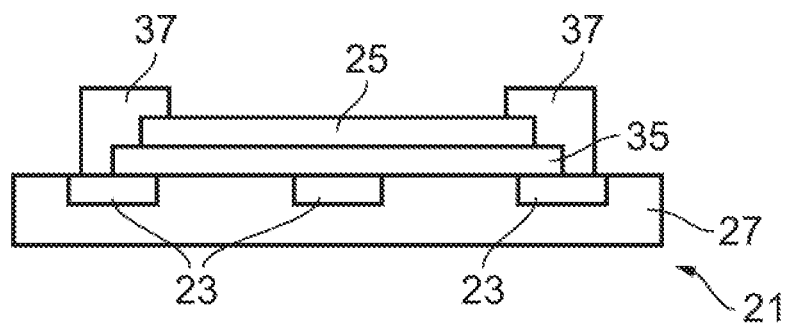

In FIG. 3F contacts 37 are provided between the source and drain electrodes 23 and the graphene. The contacts 37 may provide a direct current path between the source and drain electrodes 23 and the graphene. The contacts 37 may comprise any conductive material, such as a metal, which may be deposited between the electrodes 23 and the graphene. The contacts 37 may be deposited using photolithography, metal evaporation or any other suitable process.

Figure 3G:
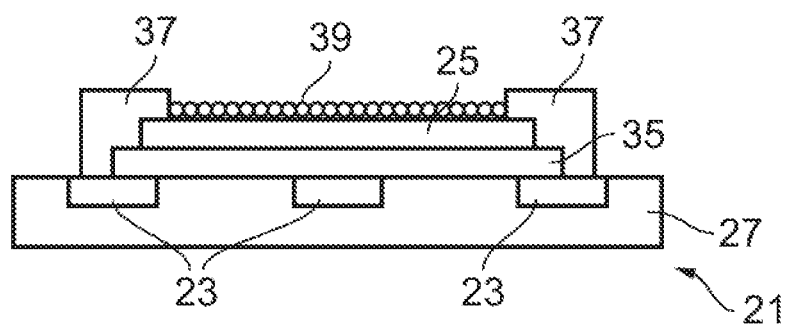

In FIG. 3G the graphene is activated. The activation of the graphene may enable the FET to be used as a sensor. The material that is used to activate the graphene may depend on the parameters that the FET is intended to detect. In the example of FIG. 3G the graphene is activated with quantum dots 39. The quantum dots 39 may be deposited using any suitable technique such as spin coating, inkjet printing, wet transfer or any other suitable process.

It is to be appreciated that variations of the method of FIGS. 3A to 3G may be made in other examples of the disclosure. For instance, in the examples of FIGS. 3A to 3G the dielectric 35 is formed on the planar surface 29 after the electrode 23 and the mouldable polymer 27 have been removed from the release layer 33. In other examples the dielectric 35 could be formed on the release layer 33. In such examples the mouldable polymer 27 would then be deposited overlaying both the dielectric 35 and the electrodes 23. This would enable the planar surface 29 to be formed from the mouldable polymer 27, the electrodes 23 and the dielectric 35. The graphene, or other two dimensional material 25, could then be deposited on the planar surface 29. This method avoids the introduction of any step edges in the connection between the electrodes 23 and the graphene. This method may be useful in apparatus 21 where the graphene layer is larger than the dielectric 35 layer.

FIGS. 4A to 4I illustrate another example method which may be used to form other example apparatus 21. In the example of FIGS. 4A to 4I the two dimensional material 25 is deposited on the release layer 33. In this example the mouldable polymer 27, the two dimensional material 25 and the embedded electrodes 23 form a planar surface 29. This may enable the two dimensional material 25 to be provided in the same plane as the electrodes 23.

Figure 4A:
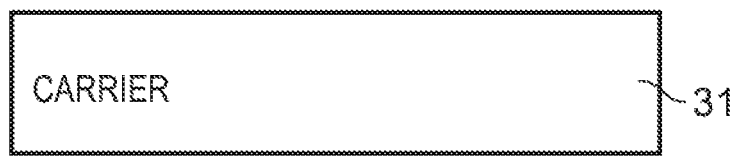

In FIG. 4A a carrier substrate 31 is provided. The carrier substrate 31 may provide a rigid or substantially rigid substrate as described above.

Figure 4B:
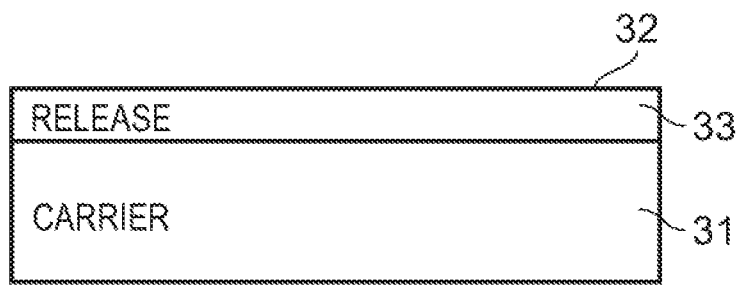

In FIG. 4B the release layer 33 is provided overlaying the carrier substrate 31. The release layer 33 may comprise a sacrificial layer with a smooth surface which may be as described above. In the examples of FIGS. 4A to 4I the release layer 33 may comprise a material such as copper which may enable graphene to be deposited onto it.

Figure 4C:
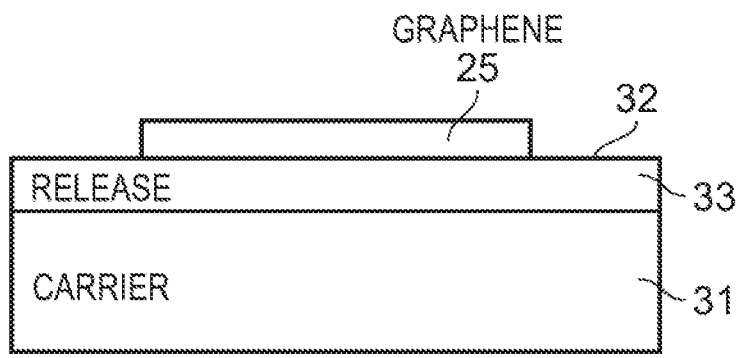

In FIG. 4C a layer of two dimensional material 25 is deposited onto the release layer 33. In the example of FIGS. 4A to 4I the two dimensional material 25 comprises graphene. Other two dimensional materials may be used in other examples of the disclosure.

The graphene may be deposited on the release layer 33 using chemical vapour deposition, a wet transfer process, a dry transfer process or any other suitable process. The graphene may be patterned on the release layer 33 in order to provide the correct channel dimensions for the apparatus 21.

Figure 4D:
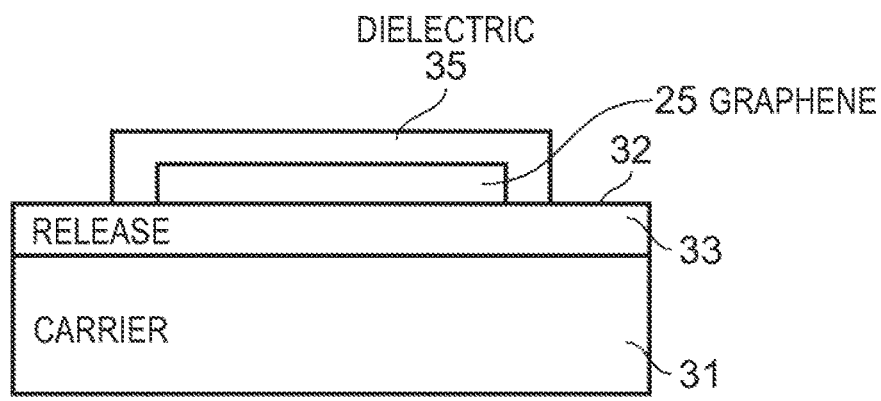

In FIG. 4D a dielectric 35 is deposited over the graphene. The dielectric 35 may be deposited so that it completely covers the graphene. In the example of FIG. 4D, where the graphene is still attached to the release layer 33, the release layer 33 and the dielectric 35 completely envelop the graphene.

The dielectric 35 may comprise any suitable insulating material. In some examples the dielectric 35 may comprise aluminum oxide which could be deposited using atomic layer deposition or any other suitable process. The dielectric 35 may be provided in a thin layer.

In some examples the graphene may be activated before the dielectric 35 is deposited. The activation of the graphene may counteract the low surface energy of the graphene and may enable uniform deposition of the dielectric 35 over the graphene. For instance, a seed layer may be evaporated onto the graphene to enable the atomic layer deposition.

Figure 4E:
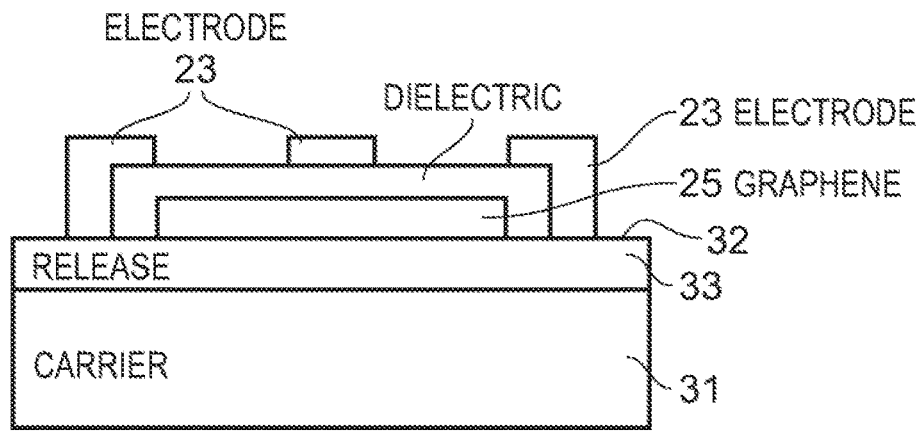

In FIG. 4E a plurality of electrodes 23 are deposited onto the release layer 33. In the example of FIGS. 4A to 4I the electrodes 23 comprise source, drain and gate electrodes. The electrodes 23 are deposited so that at least part of the electrodes 23 extend over the dielectric 35. The source and drain electrodes 23 are deposited so that at least part of the source and drain electrodes 23 are in direct contact with the surface 32 of the release layer 33. The electrodes 23 are formed so that at least the source and drain electrodes 23 are in the same plane as the graphene. This reduces the number of step edges in the apparatus 21.

The electrodes 23 may be formed using any suitable technique. For instance, in some examples the electrodes 23 may be formed by photolithography followed by evaporation of the electrode material.

Figure 4F:
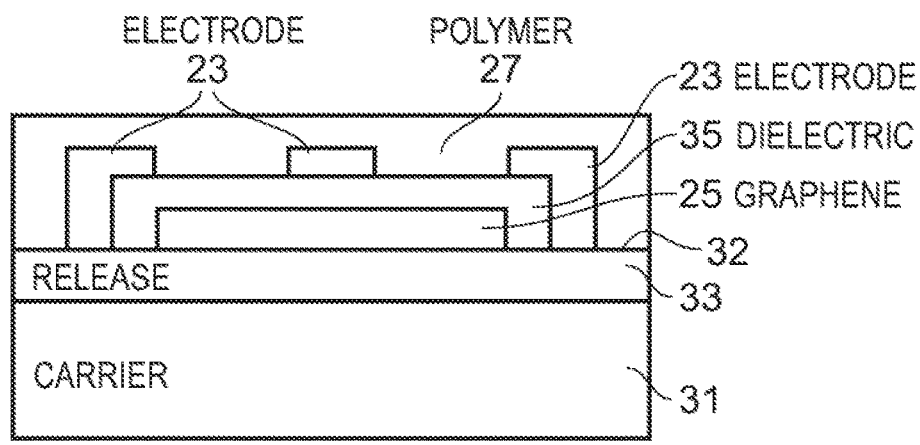

In FIG. 4F mouldable polymer 27 is provided overlaying the electrodes 23, dielectric 35 and graphene. The mouldable polymer 27 is deposited on the release layer 33 overlaying the electrodes 23, dielectric 35 and graphene. The mouldable polymer 27 comprises any polymer which will embed the electrodes 23, dielectric 35 and graphene and form a planar surface 29 against the surface 32 of the release layer 33.

In some examples the mouldable polymer 27 may comprise a liquid polymer which may be deposited onto the release layer 33 via spin coating, spray coating or any other suitable process. In other examples the mouldable polymer 27 may comprise a polymer foil which may be deposited by hot embossing or any other suitable process.

Figure 4G:
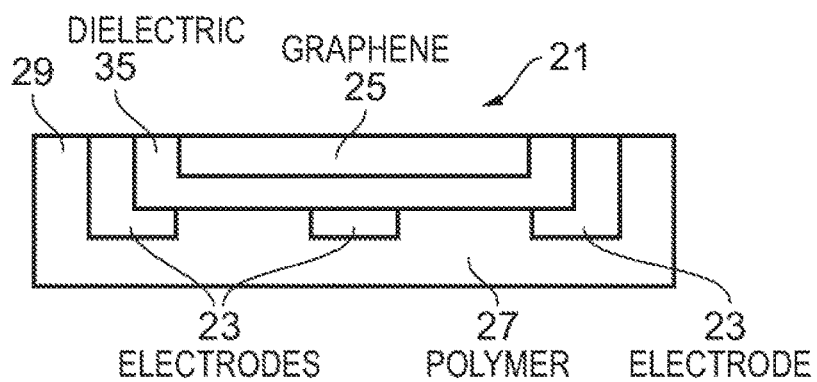

In FIG. 4G the carrier substrate 31 and release layer 33 are removed. The mouldable polymer 27 may be hardened or cured before the carrier substrate 31 and release layer 33 are removed so that the mouldable polymer 27 provides a substrate for the electrodes 23 and the graphene.

Once the release layer 33 has been removed the mouldable polymer 27, the graphene and the electrodes 23 form a planar surface 29. The planar surface 29 may be smooth and flat. The planar surface 29 may be a uniform or substantially uniform surface.

The other components of the apparatus 21 may be fabricated on the planar surface 29 formed by the mouldable polymer 27, the graphene and the electrodes 23.

Figure 4H:
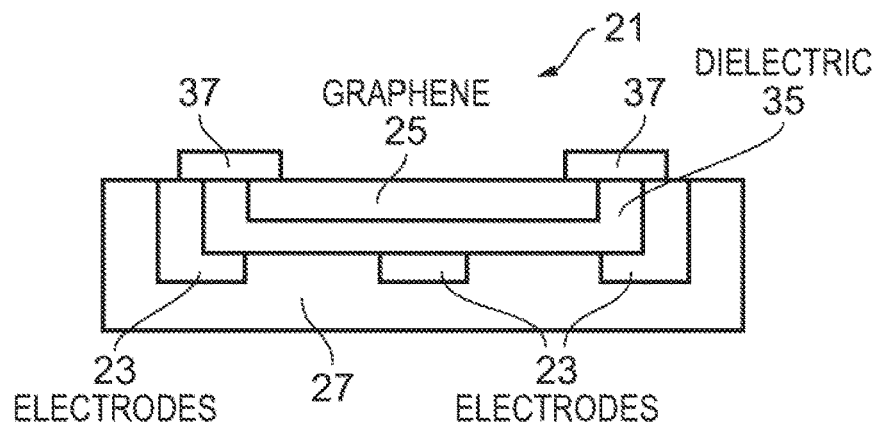

In FIG. 4H contacts 37 are provided between the source and drain electrodes 23 and the graphene. The contacts 37 may be provided on the planar surface 29. The contacts 37 may provide a direct current path between the source and drain electrodes 23 and the graphene. The contacts 37 may comprise any conductive material, such as a metal, which may be deposited between the electrodes 23 and the graphene. The contacts 37 may be deposited using photolithography, metal evaporation or any other suitable process. The contacts 37 may form a FET.

Figure 4I:
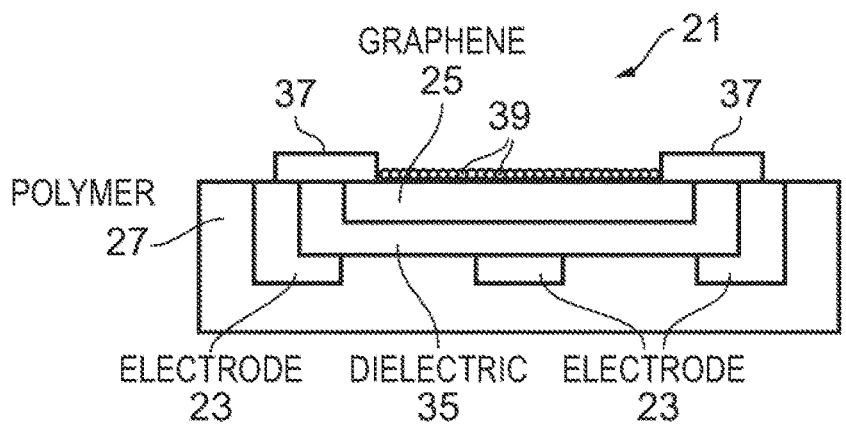

In FIG. 4I the graphene is activated. In the example of FIG. 4I the graphene is activated with quantum dots 39. The activation of the graphene may enable the FET to be used as a sensor. The material that is used to activate the graphene may depend on the parameters that the FET is intended to detect. In some examples the graphene might not be activated.

FIGS. 5A to 5K illustrate an example method which may be used to form other example apparatus 21. The example method of FIGS. 5A to 5K may be used to form apparatus 21 comprising bottom gate FET devices.

In FIG. 5A a carrier substrate 31 and a release layer 33 are provided. The carrier substrate 31 may comprise silicon, as described above, or any other suitable material. The release layer 33 is provided overlaying the carrier substrate 31. The release layer 33 may comprise a sacrificial layer with a smooth surface which may also be as described above. The release layer 33 has a smooth surface 32 on which components of an apparatus 21 can be fabricated.

In FIG. 5B a plurality of electrodes 23 are provided. The plurality of electrodes 23 form the source, gate and drain electrodes 23 of a bottom gate FET device. The plurality of electrodes 23 are deposited on the smooth surface 32 of the release layer. As the electrodes 23 are formed on the same smooth surface 32 all of the electrodes 23 are provided in the same plane. This reduces the number of step edges in the apparatus 21.

In FIGS. 5C and 5D a composite polymer substrate 53 is formed to support the plurality of electrodes 23. The composite polymer substrate 53 supports the electrodes 23 after they have been removed from the release layer 33.

In the examples of FIGS. 5A to 5K the composite polymer substrate 53 comprises two different polymers. It is to be appreciated that in some examples the composite polymer substrate 53 could comprise more than two different polymers. The at least two polymers are laminated together to form a single polymer substrate 53.

In the examples of FIGS. 5A to 5K the composite polymer substrate 53 is formed from a mouldable polymer 27 and a polymer foil 51. The mouldable polymer 27 may comprise any suitable material which will embed the electrodes 23 and form a planar surface 29 against the surface 32 of the release layer 33. The mouldable polymer 27 may comprise a thermosetting or ultra violet (UV) curable resin. This may enable the mouldable polymer 27 to be solidified after it has been deposited over the electrodes 23.

The mouldable polymer 27 may comprise a polymer resin which has a viscosity which enables the mouldable polymer 27 to embed the electrodes 23. In some examples the mouldable polymer 27 may have a viscosity of between 5 cP to 500 cP.

The mouldable polymer 27 may comprise a material which enables certain parameters to pass through. For instance, in the example of FIGS. 5A to 5K the apparatus 21 may be used as a photodetector. In such examples the mouldable polymer 27 may be transparent or at least partially transparent to visible light. It is to be appreciated that the apparatus 21 could be configured to sense other parameters in other examples of the disclosure.

The mouldable polymer 27 can be deposited on either the release layer 33 or the polymer foil 51 using any suitable technique. For instance the mouldable polymer 27 may be deposited using spin coating, bar coating, slot-die coating or any other suitable process.

After the moldable polymer 27 has been cured the moldable polymer 27 may form a thin layer. The thickness of the layer of moldable polymer 27 may be controlled by the thickness of the layer or moldable polymer 27 which is applied, the pressure applied to the apparatus 21 and the rheological properties of the moldable polymer 27. In some examples the thickness of the layer of moldable polymer 27 could be between 50 nm and 10 µm.

The mouldable polymer 27 is provided directly overlaying the electrodes. The mouldable polymer 27 is provided on the release layer 33 overlaying the electrodes 23.

The polymer foil 51 is provided overlaying the mouldable polymer 27. In the example of FIGS. 5A to 5K the mouldable polymer 27 is provided between the polymer foil 51 and the release layer 33 so that the polymer foil 51 does not directly contact the surface 32 of the release layer 33.

The polymer foil 51 may comprise a solid polymer. In some example the polymer foil 51 may comprise a flexible polymer which may deform when a user applies a force to the apparatus. The polymer foil 51 may comprise a polymer material which enables certain parameters to pass through. In examples where the apparatus 21 is used as a photodetector the polymer foil 51 may be arranged to be transparent to visible light.

For instance the polymer foil 51 may comprise a material such as polyethylene terephthalate (PET), polyethylene naphthalate (PEN), polyethersulfone (PES) or any other suitable material. Such materials may enable 90% or more of incident visibly light to pass through the polymer foil 51.

The polymer foil 51 may have a greater thickness than the layer of mouldable polymer 27. In some examples the thickness of the polymer foil 51 could be between 10 µm to 1000 µm.

FIG. 5C shows two different examples of depositing the mouldable polymer 27 and the polymer foil 51. In the first example the mouldable polymer 27 and the polymer foil 51 are deposited separately. In such examples the mouldable polymer 27 is provided overlaying the electrodes 23 and then the polymer foil 51 is provided overlaying the mouldable polymer 27.

In the second example the mouldable polymer 27 and the polymer foil 51 are deposited at the same time. In such examples the mouldable polymer 27 may be adhered to the underside of the polymer foil 51. Both the mouldable polymer 27 and the polymer foil 51 are then provided overlaying the electrodes 23.

In some examples the surfaces of different layers within the composite polymer substrate 53 may be treated to improve the adhesion between the respective layers. In some examples surface activation techniques such as plasma, corona treatments, ultraviolet/ozone (UVO) or any other suitable process could be used. In some examples adhesion promoters such as primers, self-assembled monolayers (SAM), copolymers or any other suitable material may be used.

In FIG. 5D the composite polymer substrate 53 is cured. In the example of FIG. 5D the composite polymer substrate 53 is cured using UV light. It is to be appreciated that other means of curing may be used in other examples of the disclosure. For instance in some examples the mouldable polymer 27 may comprise a thermosetting resin. In such examples the curing may comprise heating the mouldable polymer 27. The temperature to which the mouldable polymer 27 is heated may depend on the material which is used. In some examples the mouldable polymer 27 may be heated to a temperature of around 200° C.

The cured moldable polymer 27 may have a low coefficient of thermal expansion. This may prevent deformation of the apparatus 21 and ensure that the electrodes 23 remain within the same plane.

The cured moldable polymer 27 and the polymer foil 51 may have similar mechanical properties to reduce stresses and deformations within an apparatus 21. In some examples the elastic modulus and/or coefficient of thermal expansion of the cured moldable polymer 27 and the polymer foil 51 may be similar.

FIG. 5D shows two different examples of the composite polymer substrate 53. In the first example the polymer foil 51 has no additional coating. In the second example a hard coating 55 is provided on the polymer foil 51. In the example of FIG. 5D the hard coating 55 is provided on two sides of the polymer foil 51. In other examples the hard coating 55 might only be provided on one side.

The hard coating 55 may be configured to provide a barrier layer to prevent contamination of the electronic components of the apparatus 21. For instance the hard coating may prevent the ingress of oxygen, moisture or other contaminants.

In some examples the hard coating 55 may be configured to improve the absorption of a parameter which the apparatus 21 is intended to detect. For instance, where the apparatus 21 is arranged to detect visible light the hard coating 55 may comprise an antireflective coating which may improve the penetration of light into the apparatus 21.

In some examples the hard coating 55 may comprise a nanoscale coating. The nanoscale coating may comprise a material such as $SiO_x$, $SiN_x$, $AlO_x$, $AlN_x$. the hard coating 55 may be deposited on the polymer foil 51 using any suitable technique.

For instance the hard coating 55 could be deposited by atomic layer deposition, plasma enhanced chemical vapour deposition or any other suitable process.

In FIG. 5E the carrier substrate 31 and release layer 33 are removed so that the mouldable polymer 27 and the polymer foil 51 provide a composite substrate 53 for the electrodes 23.

The mouldable polymer 27 and the electrodes 23 form a planar surface 29. The planar surface 29 may be smooth and flat. The planar surface 29 may be a uniform or substantially uniform surface.

The other components of the apparatus 21 may be fabricated on the planar surface 29 formed by the mouldable polymer 27 and the electrodes 23. In FIG. 5F a dielectric 35 is provided on the planar surface 29. In the example of FIG. 3D the dielectric 35 is provided overlaying the electrodes 23.

The dielectric 35 may comprise any suitable insulating material. In some examples the dielectric 35 may comprise an inorganic oxide or nitride which could be deposited using atomic layer deposition. In other examples the dielectric 35 may comprise an organic polymer which could be deposited by a coating or printing method. The dielectric 35 may be provided in a thin layer.

Figures 5G, 5H, 5I, 5J, 5K:
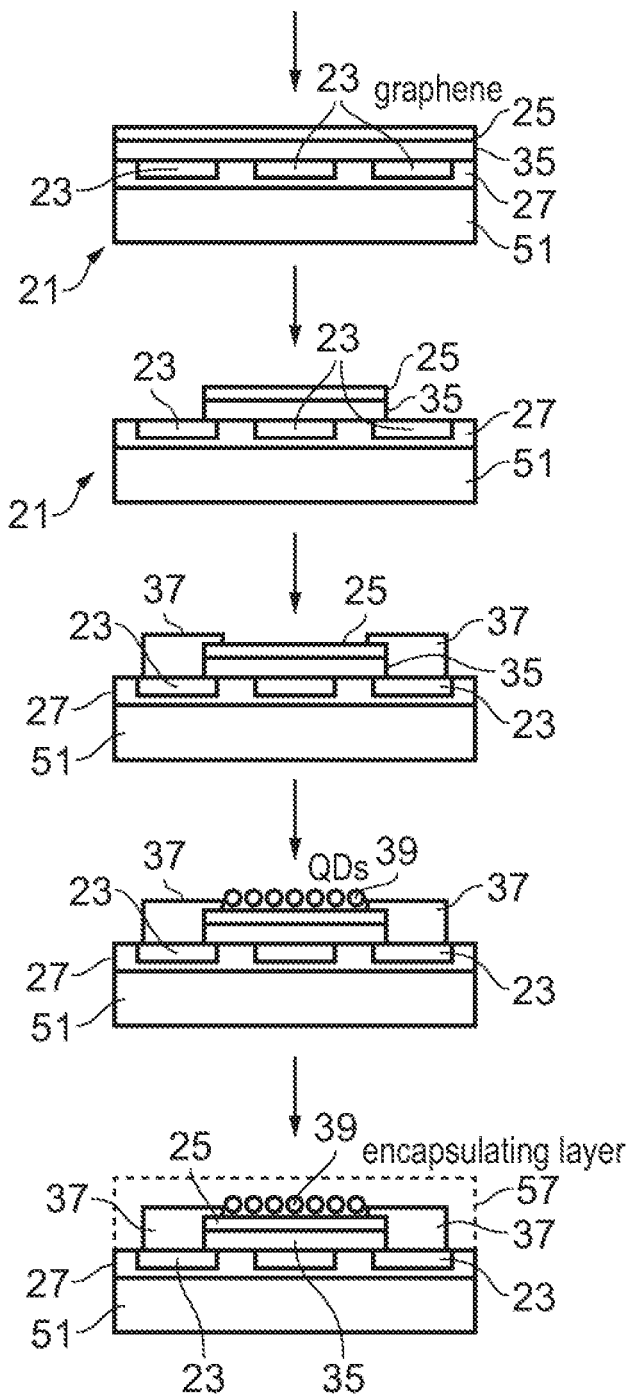
Figure 6:
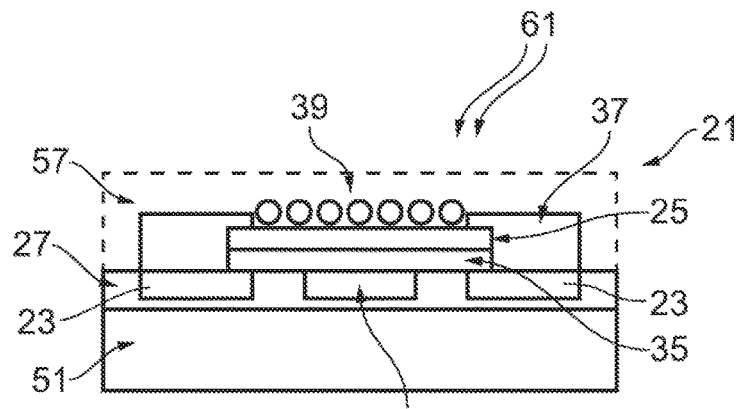

In FIG. 5G a layer of two dimensional material 25 is deposited on to the planar surface 29. In the example of FIGS. 5A to 5K the two dimensional material 25 comprises graphene.

The graphene may be deposited on to the planar surface 29 using any suitable technique. In some examples the graphene may comprise a monolayer which may be formed by chemical vapor deposition on a metal foil or any other suitable technique. The graphene monolayer may then be transferred onto the planar surface 29 using a transfer substrate, such as a poly(methyl methacrylate) (PMMA) substrate, or any other suitable process.

In the example of FIG. 5G the graphene is provided overlaying the dielectric 35 so that the dielectric 35 forms an insulating barrier between the graphene and the embedded electrodes 23.

Both the dielectric 35 and the graphene are formed on the planar surface 29 formed by the mouldable polymer 27 and the embedded electrodes 23. This allows the dielectric 35 and the graphene to be formed without any steps or discontinuities. This reduces the structural defects within the graphene and improves the electrical characteristics of the apparatus 21.

In FIG. 5H the graphene and the dielectric 35 are patterned. The graphene and the dielectric 35 may be patterned into any suitable shape. In the example of FIGS. 5A to 5K the graphene and the dielectric 35 may be patterned to enable an FET to be formed. In the example of FIG. 5H the graphene and the dielectric 35 are patterned so that at least part of the source and drain electrodes 23 are uncovered.

In FIG. 5I contacts 37 are provided between the source and drain electrodes 23 and the graphene. The contacts 37 may provide a direct current path between the source and drain electrodes 23 and the graphene. The contacts 37 may comprise any conductive material, such as a metal, which may be deposited between the electrodes 23 and the graphene. The contacts 37 may be deposited using photolithography, metal evaporation or any other suitable process.

In FIG. 5J the graphene is activated. The activation of the graphene may enable the FET to be used as a sensor. The material that is used to activate the graphene may depend on the parameters that the FET is intended to detect. In the example of FIG. 5J the graphene is activated with quantum dots 39. The quantum dots 39 may be deposited using any suitable technique such as spin coating, inkjet printing, wet transfer or any other suitable process.

In FIG. 5K an encapsulating layer is provided on the planer surface 29. The encapsulating layer 57 is provided overlaying the graphene and the contacts 37. The encapsulating layer 57 may protect the apparatus 21 from contaminants such as moisture, oxygen or other chemicals. The encapsulating layer 57 may be transparent to the parameter that the apparatus 21 is intended to detect. For instance, where the apparatus 21 is arranged to detect visible light the encapsulating layer 57 may be transparent to visible light.

The methods of FIGS. 5A to 5K enable an apparatus 21 comprising a bottom gate GFET to be formed. FIG. 6 illustrates an example apparatus 21 which has been formed by the method of FIG. 5A to 5K. In the example apparatus 21 the bottom gate GFET (graphene field effect transistor) is configured to act as a photodetector. The apparatus 21 is configured so that photons 61 which are incident on the apparatus 21 can pass through the encapsulating layer 57 and/or the polymer foil 51 and may be incident on the GFET.

In some examples the composite polymer substrate 53 may be arranged to act as a light filter. In such examples the composite polymer substrate 53 may comprise one or more polymer layers which is transparent to light in a first range of wavelengths but blocks light outside of the first range of wavelengths.

FIGS. 7A to 7K illustrate an example method which may be used to form other example apparatus 21. The example method of FIGS. 7A to 7K may be used to form apparatus 21 comprising top gate FET devices.

In FIG. 7A a carrier substrate 31 and a release layer 33 are provided. The carrier substrate 31 may comprise silicon, as described above, or any other suitable material. The release layer 33 is provided overlaying the carrier substrate 31. The release layer 33 may comprise a sacrificial layer with a smooth surface which may also be as described above. The release layer 33 has a smooth surface 32 on which components of an apparatus 21 can be fabricated.

In FIG. 7B a plurality of electrodes 23 are provided. In the example of FIG. 7B two electrodes 23 are provided. The plurality of electrodes 23 form the source and drain electrodes 23 of a top gate FET device. The plurality of electrodes 23 are deposited on the smooth surface 32 of the release layer. As the electrodes 23 are formed on the same smooth surface 32 all of the electrodes 23 are provided in the same plane. This reduces the number of step edges in the apparatus 21.

In FIG. 7C quantum dots 39 are provided on the surface 32 of the release layer 33. The quantum dots 39 may be deposited using any suitable technique such as spin coating, inkjet printing, wet transfer or any other suitable process. The quantum dots 39 are provided between the source and drain electrodes 23 and may be arranged to activate graphene which can be deposited in another block of the method.

In FIGS. 7D and 7E a composite polymer substrate 53 is formed to support the plurality of electrodes 23. The composite polymer substrate 53 may be as described above in relation FIGS. 5A to 5K. In the example of FIGS. 7D and 7E the composite polymer substrate 53 embeds both the electrodes 23 and the quantum dots 39.

In FIG. 7F the carrier substrate 31 and release layer 33 are removed so that the mouldable polymer 27 and the polymer foil 51 provide a composite substrate 53 for the electrodes 23 and the quantum dots 39.

The mouldable polymer 27 and the electrodes 23 form a planar surface 29. The planar surface 29 may be smooth and flat. The planar surface 29 may be a uniform or substantially uniform surface. The smooth flat surface may reduce the discontinuities and irregularities in the graphene that is deposited on the planar surface 29.

Figure 7G:
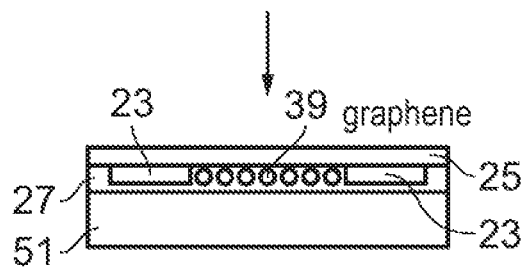

In FIG. 7G a layer of two dimensional material 25 is deposited on to the planar surface 29. In the example of FIGS. 7A to 7K the two dimensional material 25 comprises graphene.

The graphene may be deposited on to the planar surface 29 using any suitable technique. In some examples the graphene may comprise a monolayer which may be formed by chemical vapor deposition on a metal foil or any other suitable technique. The graphene monolayer may then be transferred onto the planar surface 29 using a transfer substrate, such as a poly(methyl methacrylate) (PMMA) substrate, or any other suitable process.

In the example of FIG. 7G the graphene is provided overlaying the electrodes 23 and the quantum dots 39.

Figure 7H:
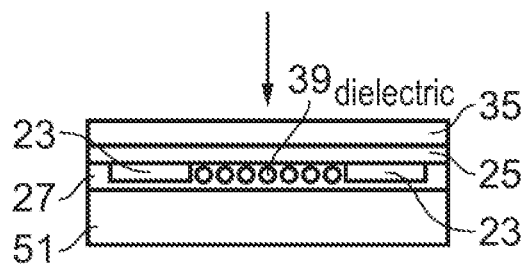

In FIG. 7H a dielectric 35 is provided overlaying the graphene. The dielectric 35 may comprise any suitable insulating material. In some examples the dielectric 35 may comprise an inorganic oxide or nitride which could be deposited using atomic layer deposition. In other examples the dielectric 35 may comprise an organic polymer which could be deposited by a coating or printing method. The dielectric 35 may be provided in a thin layer.

Both the dielectric 35 and the graphene are formed on the planar surface 29 formed by the mouldable polymer 27 and the embedded electrodes 23. This allows the dielectric 35 and the graphene to be formed without any steps or discontinuities.

This reduces the structural defects within the graphene and improves the electrical characteristics of the apparatus 21.

Figure 7I:
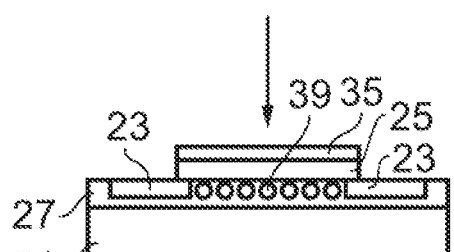

In FIG. 7I the graphene and the dielectric 35 are patterned. The graphene and the dielectric 35 may be patterned into any suitable shape. In the example of FIGS. 7A to 7K the graphene and the dielectric 35 may be patterned to enable an FET to be formed. In the example of FIG. 7I the graphene and the dielectric 35 are patterned so that at least part of the source and drain electrodes 23 are uncovered.

Figure 7J:
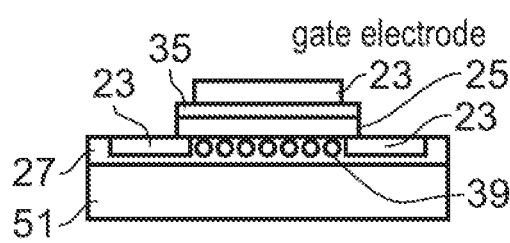

In FIG. 7J a gate electrode 23 is provided overlaying the dielectric 35. In the example of FIG. 7J the gate electrode 23 is provided overlaying the dielectric 35 so that the dielectric 35 forms an insulating barrier between the graphene and the gate electrode 23.

The gate electrode 23 may comprise any conductive material, such as a metal, which may be deposited overlaying the dielectric 35. The contacts 37 may be deposited using photolithography, metal evaporation or any other suitable process.

Figure 7K:
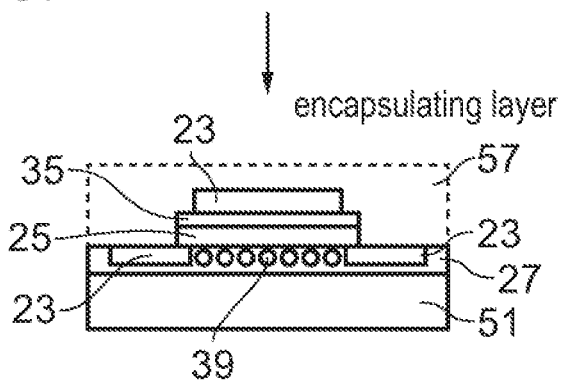

In FIG. 7K an encapsulating layer is provided on the planer surface 29. The encapsulating layer 57 is provided overlaying the graphene and the contacts 37. The encapsulating layer 57 may protect the apparatus 21 from contaminants such as moisture, oxygen or other chemicals. The encapsulating layer 57 may be transparent to the parameter that the apparatus 21 is intended to detect. For instance, where the apparatus 21 is arranged to detect visible light the encapsulating layer 57 may be transparent to visible light.

The methods of FIGS. 7A to 7K enable an apparatus 21 comprising a top gate GFET to be formed. FIG. 8 illustrates an example apparatus 21 which has been formed by the method of FIG. 7A to 7K. In the example apparatus 21 the top gate GFET (graphene field effect transistor) is configured to act as a photodetector. The apparatus 21 is configured so that photons 61 which are incident on the apparatus 21 can pass through the encapsulating layer 57 and/or the polymer foil 51 and may be incident on the GFET.

FIG. 9 illustrates an apparatus 21 which comprises top gate GFETs and bottom gate GFETs. The example methods of FIGS. 5A to 5K and 7A to 7K may be performed using the same composite substrate 53 to form an apparatus 21 such as the apparatus of FIG. 9. This enables a double sided sensor to be provided at low cost.

In the example of FIG. 9 only one top gate GFET and one bottom gate GFET is illustrated. It is to be appreciated that any number of top gate GFETs bottom gate GFETs may be provided in other examples. In some examples a plurality of apparatus 21 might be provided in an array. Some of the apparatus 21 may comprise top gate GFETs and some of the apparatus 21 may comprise bottom gate GFETs.

In the example of FIG. 9 both of the GFETs are arranged as photodetectors. It is to be appreciated that in some examples the different apparatus 21 could be arranged to detect different parameters. For instance a first GFET could be configured as a photodetector and another GFET could be configured to detect moisture or other chemicals.

Examples of the disclosure provide methods of forming apparatus 21 comprising two or more coplanar electrodes 23 and a channel of two dimensional material 25. Having at least the two electrodes 23 in the same plane reduces the number of steps or other discontinuities in the two dimensional material 25 which reduces the number of defects within the two dimensional material 25. Reducing the number of defects within the two dimensional material 25 increases carrier mobility within the channel of two dimensional material 25 and provides for an improved apparatus 21.

Examples of the disclosure also provide smooth flat surfaces for the deposition of graphene or other two dimensional material 25. Having a smooth flat surface reduces a number of factors which can reduce the carrier mobility in the two dimensional material such as defects in the two dimensional material 25, contamination of the two dimensional material 25, charge concentrations in the substrate supporting the two dimensional material 25, water or other contaminants trapped between the two dimensional material 25 and the substrate and other similar factors. Having a smooth flat surface for the deposition of graphene or other two dimensional material 25 also allows for good contact between the two dimensional material 25 and dielectric 35 or electrode 23.

In some examples the embedding of components such as electrodes 23, two dimensional material 25 and dielectric 35 can be used to control the position of the components relative to the neutral plane. As the apparatus 21 can be very thin the components of the apparatus 21 can be positioned very close to the neutral axis of the apparatus 21. This may provide for a more resilient apparatus 21 and may enable strain sensitive components to be protected when the apparatus 21 is bent or otherwise deformed. This may also enable the apparatus 21 to be bent to a higher degree of curvature.

Examples of the disclosure which use a composite polymer substrate 53 may provide for improved transparency to parameters such as visible light. As the mouldable polymer 27 is adhered to a polymer foil 51 to provide a composite substrate only a thin layer of the mouldable polymer 27 is needed. The polymer foil 51 may comprise a material which is transparent to a parameter which is to be detected by the apparatus 21. This allows for both transparency and mechanical flexibility.

The use of a composite polymer substrate 53 enables different polymers to be used for different apparatus 21. This allows the polymers to be chosen to address the requirements of the apparatus 21 that is being formed and/or the parameters that the apparatus 21 is intended to detect.

The methods of the disclosure may enable large numbers of apparatus 21 to be produced at low costs. The method may be fast as processes such as curing may only take several seconds to be completed. The method may avoid the use of high temperatures which could damage sensitive components. For instance the thermosetting resins may be set at temperatures of 200° C. which may be low enough to avoid damaging other components of the apparatus 21.

In the above description the term "coupled" means operationally coupled. Any number of intervening components may be provided including no intervening components.

The term "comprise" is used in this document with an inclusive not an exclusive meaning. That is any reference to X comprising Y indicates that X may comprise only one Y or may comprise more than one Y. If it is intended to use "comprise" with an exclusive meaning then it will be made clear in the context by referring to "comprising only one . . ." or by using "consisting".

In this brief description, reference has been made to various examples. The description of features or functions in relation to an example indicates that those features or functions are present in that example. The use of the term "example" or "for example" or "may" in the text denotes, whether explicitly stated or not, that such features or functions are present in at least the described example, whether described as an example or not, and that they can be, but are not necessarily, present in some of or all other examples. Thus "example", "for example" or "may" refers to a particular instance in a class of examples. A property of the instance can be a property of only that instance or a property of the class or a property of a sub-class of the class that includes some but not all of the instances in the class. It is therefore implicitly disclosed that a features described with reference to one example but not with reference to another example, can where possible be used in that other example but does not necessarily have to be used in that other example.

Although embodiments of the present invention have been described in the preceding paragraphs with reference to various examples, it should be appreciated that modifications to the examples given can be made without departing from the scope of the invention as claimed.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

We claim:

1. A method for forming a field effect transistor, said method comprising:
   providing a release layer with a smooth surface on a carrier substrate;
   depositing source, gate and drain electrodes on the release layer;
   depositing a mouldable polymer overlaying the source, gate and drain electrodes on the release layer, so that the source, gate and drain electrodes and the mouldable polymer form a planar surface against the smooth surface of the release layer;
   removing the carrier substrate and the release layer;
   providing a dielectric on the planar surface overlying the gate electrode and at least part of the source and drain electrodes;
   depositing a layer of two dimensional material on the dielectric;
   providing a first contact between the source electrode and the two dimensional material so that the contact provides a direct current path between the source electrode and the two dimensional material; and
   providing a second contact between the drain electrode and the two dimensional material so that the contact provides a direct current path between the drain electrode and the two dimensional material.

2. The method according to claim 1, wherein the two dimensional material comprises graphene.

3. The method according to claim 1, wherein the two-dimensional material is activated with quantum dots.

4. The method according to claim 1, wherein, before the contacts are provided, the two-dimensional material and the dielectric are patterned so that at least part of the source and drain electrodes are uncovered.

5. The method according to claim 1, further comprising providing a plurality of electrodes and portions of two dimensional materials to form a plurality of field effect transistors, wherein at least some the field effect transistors are bottom gate field effect transistors and at least some of the field effect transistors are top gate field effect transistors.

6. A method for forming a field effect transistor, said method comprising:
   providing a release layer with a smooth surface on a carrier substrate;
   depositing source and drain electrodes on the smooth surface of the release layer;
   depositing quantum dots between the source and drain electrodes on the smooth surface of the release layer;
   depositing a mouldable polymer overlaying the source and drain electrodes on the release layer, so that the source and drain electrodes and the mouldable polymer form a planar surface against the smooth surface of the release layer;
   removing the carrier substrate and the release layer;
   depositing a layer of two dimensional material on the planar surface;
   providing a dielectric on the two dimensional material;
   patterning the two-dimensional material and the dielectric so that at least part of the source and drain electrodes are uncovered; and
   providing a gate electrode overlaying the dielectric.

7. The method according to claim 6, wherein the two dimensional material comprises graphene.

8. The method according to claim 6, further comprising providing a plurality of electrodes and portions of two dimensional materials to form a plurality of field effect transistors wherein at least some the field effect transistors are bottom gate field effect transistors and at least some of the field effect transistors are top gate field effect transistors.

* * * * *